(12) United States Patent
Duffy (10) Patent No.: US 9,452,047 B2
(45) Date of Patent: Sep. 27, 2016

(54) HEART VALVE PROSTHESIS RECAPTURE DEVICES

(75) Inventor: Niall Duffy, Ballybrit (IE)

(73) Assignee: Medtronic Vascular Galway, Ballybrit, Galway (IE)

( * ) Notice: Subject to any disclaimer, the term of this patent is extended or adjusted under 35 U.S.C. 154(b) by 66 days.

(21) Appl. No.: 13/440,372

(22) Filed: Apr. 5, 2012

(65) Prior Publication Data
US 2013/0268064 A1 Oct. 10, 2013

(51) Int. Cl.
*A61F 2/24* (2006.01)
*A61F 2/95* (2013.01)

(52) U.S. Cl.
CPC ...... *A61F 2/2436* (2013.01); *A61F 2002/9534* (2013.01); *A61F 2250/0018* (2013.01); *A61F 2250/0036* (2013.01); *A61F 2250/0039* (2013.01)

(58) Field of Classification Search
CPC ............... A61F 2002/9534; A61F 2250/0039; A61F 2/2436
USPC ................................ 623/2.11; 606/200, 127
See application file for complete search history.

(56) References Cited

U.S. PATENT DOCUMENTS

| | | | |
|---|---|---|---|
| 5,683,451 A * | 11/1997 | Lenker et al. | 623/1.11 |
| 5,824,041 A | 10/1998 | Lenker et al. | |
| 5,997,508 A | 12/1999 | Lunn et al. | |
| 6,001,118 A * | 12/1999 | Daniel et al. | 606/200 |
| 6,964,670 B1 * | 11/2005 | Shah et al. | 606/200 |
| 8,313,525 B2 * | 11/2012 | Tuval et al. | 623/2.11 |
| 2006/0195118 A1 * | 8/2006 | Richardson | 606/113 |
| 2008/0147181 A1 | 6/2008 | Ghione et al. | |
| 2008/0188928 A1 * | 8/2008 | Salahieh et al. | 623/2.11 |
| 2009/0069889 A1 * | 3/2009 | Suri et al. | 623/2.11 |
| 2009/0171456 A1 | 7/2009 | Kveen et al. | |
| 2009/0281619 A1 * | 11/2009 | Le et al. | 623/2.11 |
| 2010/0049313 A1 | 2/2010 | Alon et al. | |
| 2011/0245917 A1 | 10/2011 | Savage et al. | |

FOREIGN PATENT DOCUMENTS

| | | |
|---|---|---|
| WO | WO2007/035471 | 3/2007 |
| WO | WO2009/026272 | 2/2009 |
| WO | WO2011/035327 | 3/2011 |

\* cited by examiner

*Primary Examiner* — Corrine McDermott
*Assistant Examiner* — Sarah Simpson (57) ABSTRACT

Heart valve prosthesis recapture devices and methods for recapture are disclosed, which can be used for recapturing a partially deployed heart valve prosthesis. The recapture device comprises a recapture sleeve, configured to envelop and collapse a partially deployed heart valve prosthesis. The recapture sleeve comprises a distal end, configured to be securely attached to a guide wire, and a proximal end, comprising an opening along a longitudinal axis of the recapture sleeve. The opening can be configured to expand as it engages the heart valve prosthesis, and be biased toward a closed configuration. An attachment element can interface with the distal end of the recapture sleeve and be securely attached to a guide wire, such as by crimping. The recapture sleeve can include a support structure comprising at least one spine and a plurality of ribs.

11 Claims, 5 Drawing Sheets

HEART VALVE PROSTHESIS RECAPTURE DEVICES

BACKGROUND OF THE INVENTION

1. Field of the Invention

The present invention relates to devices and methods for recapturing partially deployed heart valve prostheses within a body lumen. The recapture devices include a recapture sleeve attached to a guide wire at its distal end, with an opening along a longitudinal axis of the recapture sleeve at the proximal end of the recapture sleeve.

2. Background

Recently, minimally invasive approaches have been developed to facilitate catheter-based implantation of prostheses, for example, transcatheter aortic-valve prosthesis implantation. Typically, during transcatheter prosthesis implantations, a prosthesis is radially contracted onto a delivery catheter so that the prosthesis can be introduced into a body lumen, for example, into the femoral artery, the subclavian artery, or the aorta, or into a body cavity, for example, a chamber of the heart (e.g., the ventricle). The contracted configuration of the prosthesis on the delivery catheter can be maintained by a retaining sleeve positioned over the prosthesis. Using the delivery catheter, the prosthesis can be guided to a desired implantation site through the body lumen or body cavity. Once the prosthesis is advanced to the desired implantation site, the prosthesis can be deployed by withdrawing the retaining sleeve and allowing the prosthesis to expand, for example, through balloon expansion or self-expansion.

During transapical deployment of an aortic heart valve prosthesis, a problem can occur if during the final stages of deployment the prosthetic valve moves distal to the native valve (i.e. toward the aortic arch). At this stage of deployment, the prosthetic valve will be partially expanded, making it difficult to reposition it within the native valve. In a transfemoral procedure, for instance, the prosthesis can be forced back into the introducer in order to remove it from the body. However, this cannot be done in a transapical procedure. Therefore, a system or device is needed to recapture a partially deployed heart valve prosthesis implanted via a transapical procedure.

BRIEF SUMMARY OF THE INVENTION

The present invention provides a heart valve prosthesis recapture device including a recapture sleeve attached to a guide wire. The distal end of the recapture sleeve can be attached to the guide wire, such as by crimping it to the guide wire. The proximal end of the recapture sleeve can have an opening along a longitudinal axis of the recapture sleeve, which can expand to envelop a partially deployed heart valve prosthesis. In the event that the heart valve prosthesis is incorrectly deployed, the guide wire with attached recapture sleeve can be moved in a proximal direction to encompass the distal end of the heart valve prosthesis, and further moved in the proximal direction to collapse and capture the heart valve prosthesis within the recapture sleeve. The heart valve prosthesis can be repositioned and redeployed, or removed from the body.

Generally, the heart valve prosthesis recapture device includes a heart valve prosthesis recapture sleeve configured to envelop and collapse a partially deployed heart valve prosthesis within a body lumen. The recapture sleeve generally includes a distal end configured to be securely attached to a guide wire and a proximal end including an opening along a longitudinal axis of the recapture sleeve.

A method of recapturing a partially deployed heart valve prosthesis generally includes inserting a heart valve prosthesis recapture device including a recapture sleeve securely attached to a guide wire into a body, delivering a heart valve prosthesis to a location in the body proximal to the recapture sleeve, at least partially deploying the heart valve prosthesis, moving the guide wire in a proximal direction to envelop at least part of the heart valve prosthesis within the recapture sleeve, and capturing the heart valve prosthesis within the recapture sleeve.

BRIEF DESCRIPTION OF THE FIGURES

The accompanying figures, which are incorporated herein, form part of the specification and illustrate embodiments of heart valve prosthesis recapture devices and methods for recapturing a heart valve prosthesis with a recapture device. Together with the description, the figures further serve to explain the principles of and to enable a person skilled in the relevant art(s) to make and use the recapture devices and methods described herein. In the drawings, like reference numbers indicate identical or functionally similar elements.

DETAILED DESCRIPTION OF THE INVENTION

The following detailed description of heart valve prosthesis recapture devices and methods of recapturing a heart valve prosthesis refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent to one of skill in the art that the devices and methods described below can be implemented in many different embodiments of hardware. Any actual hardware described is not meant to be limiting. The operation and behavior of the devices and methods presented are described with the understanding that modifications and variations of the embodiments are possible given the level of detail presented.

Figure 1A:
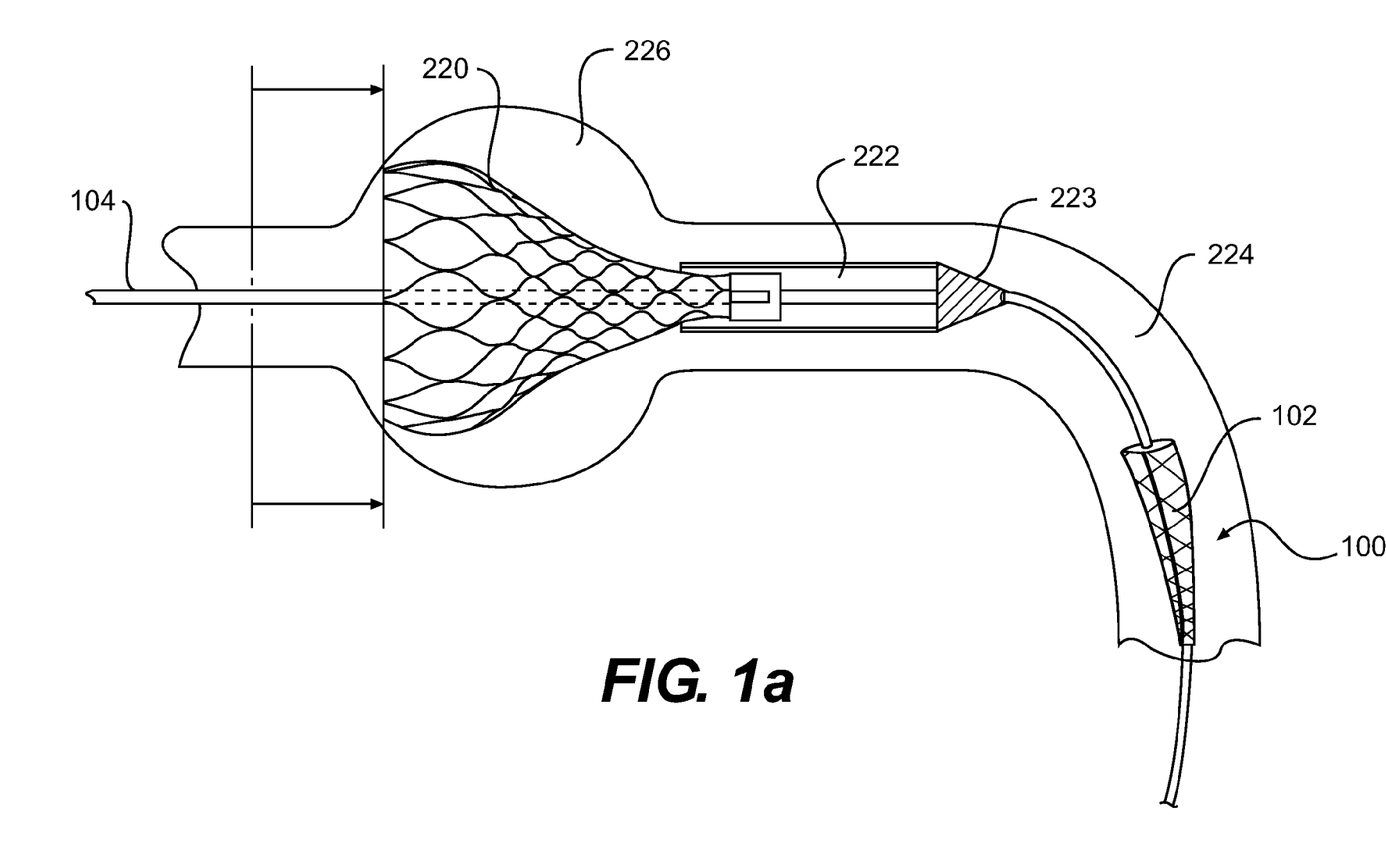
FIG. 1a illustrates a partially deployed heart valve prosthesis within a body lumen and a recapture device attached to a wire.

FIG. 1a illustrates one embodiment of a heart valve recapture device 100 prior to its use during a transapical procedure. The recapture sleeve 102 has been attached to the guide wire 104 and, in this embodiment, is in a closed or wrapped down configuration. The heart valve prosthesis 220 is partially deployed from the capsule 222, but has moved distally from the desired deployment position, as indicated by the arrows.

Figure 1B:
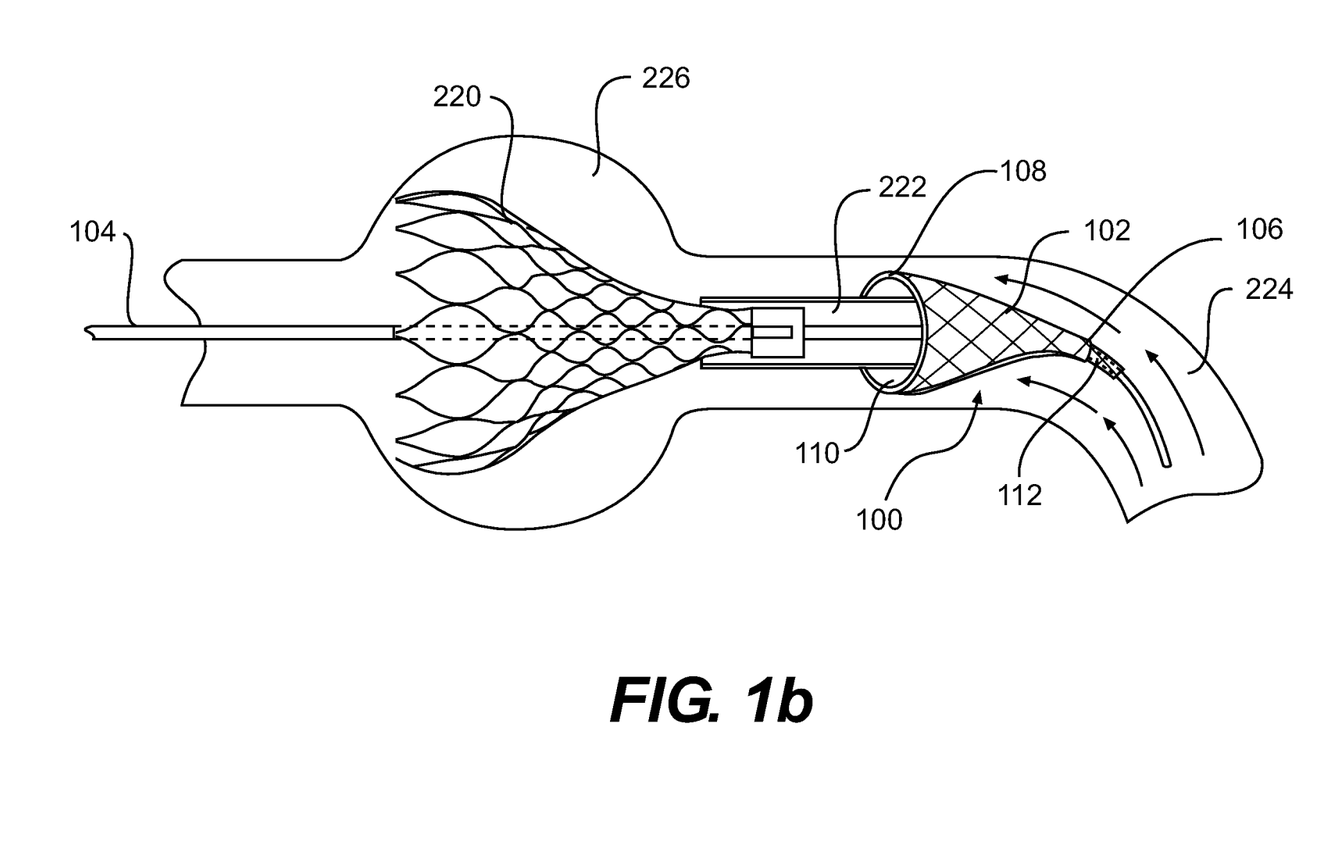
FIG. 1b illustrates a recapture device being moved in a proximal direction to begin recapturing a partially deployed heart valve prosthesis.

FIG. 1b illustrates a heart valve recapture device 100 in accordance with one embodiment presented herein. Generally, the recapture sleeve 102 can be attached to a guide wire 104 at an attachment point 112 at the distal end 106 of the recapture sleeve 102. The recapture sleeve 102 can have an opening 110 at the proximal end 108 of the recapture sleeve 102 into which the heart valve prosthesis 220 can enter as the recapture sleeve 102 is moved in the proximal direction.

Figure 1C:
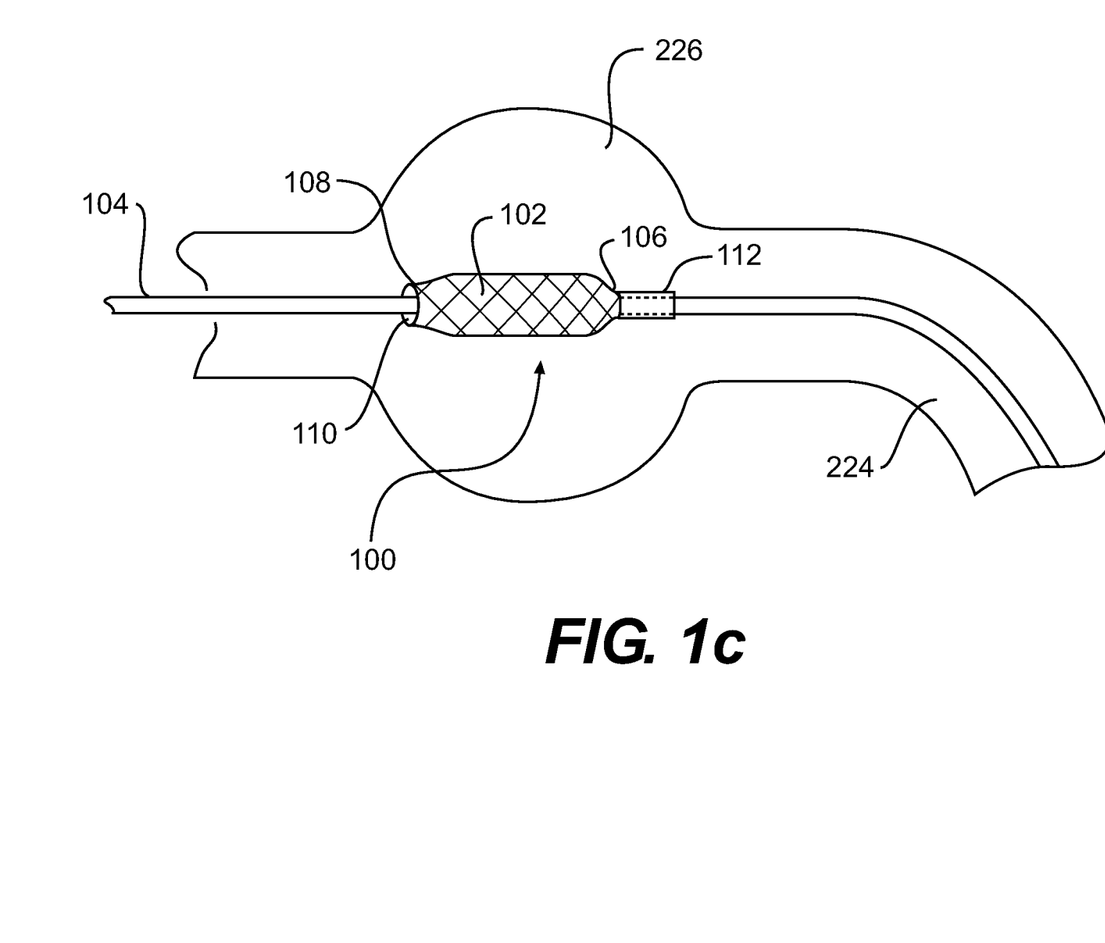
FIG. 1c illustrates a recapture device after recapturing a heart valve prosthesis.

FIG. 1c illustrates a heart valve recapture device 100 after recapturing a heart valve prosthesis 220 (not shown). The entire heart valve prosthesis 220 has been enveloped within the recapture sleeve 102, and the heart valve prosthesis 220 has been collapsed down. In the illustrated embodiment, the opening 110 at the proximal end 108 has closed down to a tapered profile, which facilitates repositioning or removal from the body.

Generally, the recapture sleeve 102 can be the main element of the recapture device 100 responsible for recapturing a partially deployed heart valve prosthesis 220. The recapture sleeve 102 can have an opening 110 at the proximal end 108 along the longitudinal axis of the recapture sleeve 102. In certain embodiments, the opening 110 can be in a closed position until the recapture sleeve 102 is needed, if at all. Additionally, in certain embodiments the recapture sleeve 102 itself can be radially constrained about the guide wire 104, such as by a wire wrap similar to those used with a PTCA balloon, which can be released if it is necessary to use the recapture sleeve 102.

The recapture sleeve 102 is generally configured to envelop the heart valve prosthesis 220. Generally, at least the opening 110 at the proximal end 108 of the recapture sleeve 102 is radially expandable. The expansion of the opening 110 and the recapture sleeve 102 can be limited, such as by a physical constraint or material properties. In certain embodiments, the opening 110 can collapse back down after the recapture sleeve 102 envelops the heart valve prosthesis 220, as a result of its material properties or through physical manipulation. The remainder of the recapture sleeve 102 should have sufficient stiffness to radially collapse the heart valve prosthesis 220 as it enters the recapture sleeve 102. The force required to accomplish this can be significant, as the heart valve prosthesis 220 is generally made from self-expanding metal designed to remain in its expanded form at higher temperatures, such as those within a body lumen. However, the forces placed on the heart valve prosthesis 220 during the recapture procedure should not be so great as to damage the heart valve prosthesis 220 if it is to be redeployed.

There are many possible embodiments for the recapture sleeve 102. The recapture sleeve 102 can be made from a single material or it can include multiple materials. Generally, the material of the proximal end 108 should allow the recapture sleeve 102 to expand upon contact with the heart valve prosthesis 220 and collapse back down after the heart valve prosthesis 220 is enveloped within the recapture sleeve 102. Generally, the material of the distal end 106 should be stiff enough to collapse the heart valve prosthesis 220 as it is enveloped by the recapture sleeve 102.

In certain embodiments, the recapture sleeve 102 can be made from a single material, including conventional polymeric materials generally used in the field for catheters, introducers and sheaths. In certain embodiments, the recapture sleeve 102 can be made from a wire braid, woven fabric or metal, which generally can be covered by a polymer coating. If made from a single material, the recapture sleeve 102 can be fabricated such that the proximal end 108 and the distal end 106 have different material properties. For example, the proximal end 108 can be thinner or more elastic, whereas the distal end 106 can be thicker or stiffer. This can facilitate recapture of the heart valve prosthesis 220 by allowing the proximal end 108 to expand as it engages the heart valve prosthesis 220, whereas the stiffness of the distal end 106 helps collapse the heart valve prosthesis 220 as it is enveloped by the recapture sleeve 102. In certain embodiments, the material properties of the recapture sleeve 102 can change along a gradient, for example, becoming gradually stiffer from the proximal end 108 to the distal end 106.

Alternatively, the recapture sleeve 102 can be made from multiple materials. The materials can be connected to each other such as by weaving or stitching. For example, the proximal end 108 can be made of an elastic material to allow the opening 110 to expand as it engages the heart valve prosthesis 220, and the distal end 106 can be made of a stiff material capable of collapsing the heart valve prosthesis 220 as it is enveloped by the recapture sleeve 102. In certain embodiments, there can be a transition zone between the proximal end 108 and distal end 106, which can exhibit material properties of each respective end.

The stiffness of at least part of the recapture sleeve 102 should be such that the inward force is sufficient to radially collapse the heart valve prosthesis 220 as it is enveloped by the recapture sleeve 102. In certain embodiments, the necessary stiffness can be a result of the material composition of the recapture sleeve 102 itself. Suitable materials for the recapture sleeve 102 include the materials traditionally used to make catheters, and can include by way of example, polymers, wire mesh, expandable metal, elastic materials, woven fabric and composites. Generally, expansion of the recapture sleeve 102 can be limited, such as by physical properties or support structures, discussed below, such that the heart valve prosthesis 220 is forced to collapse as it is enveloped by the recapture sleeve 102.

In certain embodiments, the recapture sleeve 102 can include a support structure. The support structure can include at least one spine structure and a plurality of reinforcing elements, such as ribs. The ribs can be curved structures and can be attached to the spine. The ribs can be any shape, including circular, semi-circular or "U"-shaped. To facilitate recapturing and collapsing the heart valve prosthesis 220, the sizing and spacing of the ribs and spine structures can be designed such that they provide less stiffness at the proximal end 108 of the recapture sleeve 102 and more stiffness at the distal end 106. Such variable stiffness can also be accomplished using different materials for ribs located at various positions along the recapture sleeve 102.

In certain embodiments, the recapture sleeve 102 can be in the shape of a funnel or cone, where the diameter of the recapture sleeve 102 can gradually decrease from the proximal end 108 to the distal end 106. The recapture sleeve 102 can comprise a support structure, such as wire mesh, with an inner covering or an outer covering, or both an inner and outer covering. The coverings can be lubricated with a biocompatible lubricant or hydrophilic coating to reduce friction between the recapture sleeve 102 and the heart valve prosthesis 220. Alternatively, the interior surface of the recapture sleeve 102 can be a naturally low-friction surface such as a silicon or Teflon (PTFE) material.

Generally, the opening 110 of the recapture sleeve 102 can be located at the proximal end 108 of the recapture sleeve 102 along a longitudinal axis of the recapture sleeve 102.

Figure 2A:
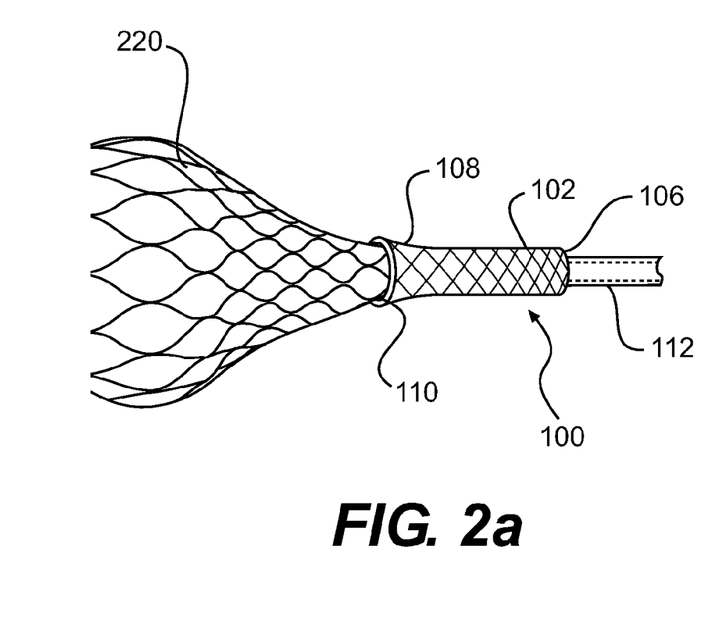
FIG. 2a illustrates the proximal end of a recapture sleeve flared radially outward and elastically expanded to recapture a heart valve prosthesis.

The opening 110 can allow the recapture sleeve 102 to envelop a partially deployed heart valve prosthesis. Because the recapture sleeve 102 should generally fit over both the capsule 222 and the heart valve prosthesis 220, the initial diameter of the opening 110 can generally be greater than the distal end 223 of the capsule 222. The opening 110 should generally be able to expand to a diameter greater than that of the capsule 222 so that the recapture sleeve 102 can envelop the heart valve prosthesis 220, as illustrated in FIG. 1b. In order to radially expand when engaging the capsule 222 and heart valve prosthesis 220, the opening 110 can be made of an elastic material. The ability to expand can allow the recapture sleeve 102 to envelop the partially deployed heart valve prosthesis, which has a diameter greater than that of the capsule 222 used to constrain it prior to deployment. In certain embodiments, the opening 110 can be flared radially outward in the shape of a funnel, as shown in FIG. 2a. This can reduce the forces on the opening 110 as the recapture sleeve 102 envelops the heart valve prosthesis 220, facilitating recapture. Initially, the funnel-shaped opening 110 can be radially constrained, such as by a wire wrap, which can be released if recapture of the heart valve prosthesis 220 is necessary. In other embodiments, the funnel-shaped opening 110 is biased towards an initial closed configuration.

Figure 2B:
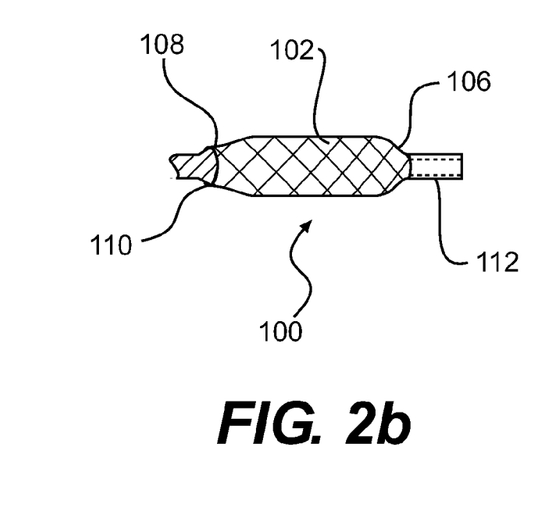
FIG. 2b illustrates the proximal end of a recapture sleeve collapsed back down after recapturing a heart valve prosthesis.

Further, as illustrated in FIG. 2b, in certain embodiments the opening 110 can close back down after enveloping the heart valve prosthesis 220. The opening 110 can be biased in a closed position by configuring a shape memory of the material, such as by heat forming the opening in a closed position. This can cause the opening to return to a closed position after expanding to envelop the heart valve prosthesis 220. In other embodiments, a spring element is incorporated into the proximal opening 110 to bias it towards the closed position.

Physical manipulation can be used to radially expand and contract the opening 110. In one such embodiment, a drawstring element, such as a wire or string, can be manipulated to increase or decrease the diameter of the opening 110. Initially, the opening 110 can be at least partially closed, and in some embodiments fully closed. By releasing the drawstring, the diameter of the opening 110 can be increased. Once the heart valve prosthesis 220 is recaptured within the recapture sleeve 102, the drawstring can be manipulated so that the diameter of the opening 110 can be made smaller. Closing the opening 110 can also facilitate collapsing the heart valve prosthesis 220.

The recapture sleeve 102 can be attached to the guide wire 104 at an attachment point 112 in any manner that will ensure the recapture sleeve 102 is secured to the guide wire 104 to withstand the force of recapturing the heart valve prosthesis 220. In one embodiment, a laser cut metal tube can be crimped to the guide wire 104 about the distal end 106 of the recapture sleeve 102 at the attachment point 112. If the recapture sleeve 102 itself is metal, the distal end 106 can be crimped directly to the guide wire 104. In other embodiments, the recapture sleeve 102 can be welded to the guide wire 104 at the attachment point 112. In further embodiments, a biocompatible adhesive can be used to attach the recapture sleeve 102 to the guide wire 104. In certain embodiments, an attachment element can interface with the recapture sleeve 102, and the attachment element can be secured to the guide wire 104. The guide wire 104 itself can be made from any material generally used in the field for guide wires that aid the travel of catheters through the vascular system.

FIGS. 2a and 2b illustrate certain embodiments of the recapture device 100. FIG. 2a illustrates an embodiment where the opening 110 at the proximal end 108 of the recapture sleeve 102 is flared radially outward. This embodiment also illustrates an elastic opening 110 expanding to envelop the heart valve prosthesis 220. The recapture sleeve 102 can be more elastic at the proximal end 108 to help the recapture sleeve 102 envelop the heart valve prosthesis 220, and less elastic at the distal end 106 to help collapse the heart valve prosthesis 220 as the recapture sleeve 102 envelops the heart valve prosthesis 220. FIG. 2b illustrates an embodiment where the opening 110 is radially collapsed after enveloping the heart valve prosthesis 220. Such a tapered configuration can help safely reposition or remove the heart valve prosthesis 220 without damaging the interior walls of the aortic sinus 226 or the aorta 224. Alternatively, the opening 110 can be mechanically closed, such as by manipulating a drawstring element, after the recapture sleeve 102 envelops the heart valve prosthesis 220.

Figure 3:
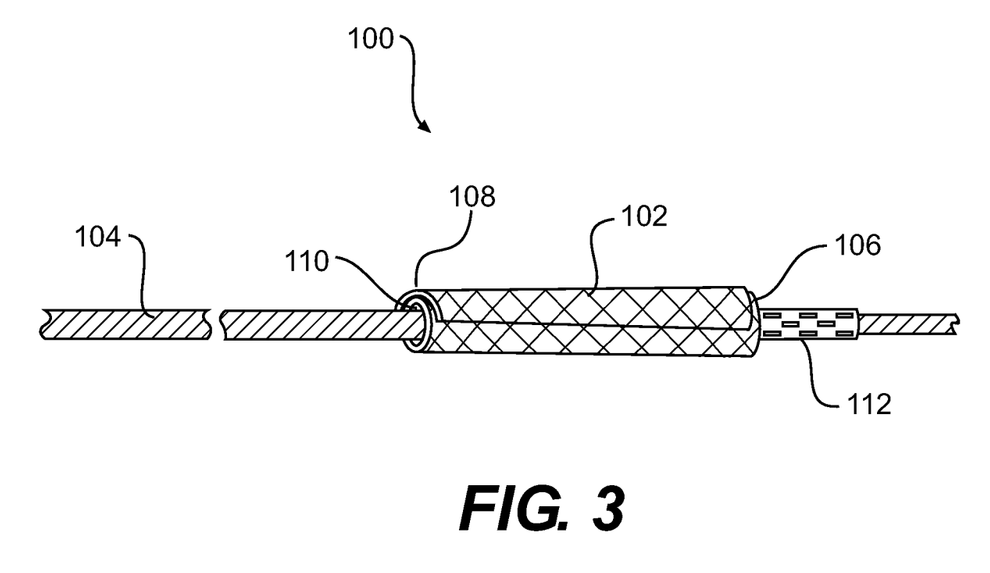
FIG. 3 illustrates one embodiment of a recapture device attached to a guide wire.

FIG. 3 illustrates an alternative embodiment of the recapture device 100. In certain embodiments, the recapture sleeve 102 can be an expandable tube, where a portion of the tube can be folded over itself, such as disclosed in U.S. Pat. No. 5,997,508 to Lunn et al, herein incorporated by reference in its entirety. As the recapture sleeve 102 engages the partially deployed heart valve prosthesis 220, the force can cause the folds in the expandable tube to open, thereby increasing the diameter of the recapture sleeve 102, yet maintaining its structural rigidity. In an alternative embodiment, the recapture sleeve 102 can include at least one, but generally less than four, layers of wrapped material, such as plastic, wire mesh or woven fabric. The wrapped layers can allow the recapture sleeve 102 to expand as it engages the heart valve prosthesis 220, yet be configured to prevent expansion of the recapture sleeve 102 beyond a desired diameter in order to provide enough inward force to collapse the heart valve prosthesis 220. Structural reinforcement elements, such as ribs along the recapture sleeve 102, can also limit the expansion of the recapture sleeve 102. In certain embodiments, a coil can run within the layers to provide structural support. In other embodiments, the recapture sleeve 102 can have a shape memory, which generates the force used to collapse the recaptured heart valve prosthesis 220. An attachment element, such as a laser cut metal tube, can be crimped about the distal end 106 of the recapture sleeve 102 and the guide wire 104 at an attachment point 112 to secure the recapture sleeve 102 to the guide wire 104. Alternatively, the attachment element can interface with the distal end 106 of the recapture sleeve 102, and itself be secured to the guide wire 104.

FIGS. 1a-1c generally illustrate one method of recapturing a partially deployed heart valve prosthesis 220 that is within the aorta 224 and aortic sinus 226. Prior introducing the recapture device 100 and heart valve prosthesis 220 into the patient, the patient is prepared for the procedure, which generally includes anesthesia and making an incision between the patient's ribs for transapical access to the heart. The recapture sleeve 102 can be attached to the guide wire 104, such as by crimping, prior to the procedure, or the recapture sleeve 102 can be a prefabricated attachment on the guide wire 104. Generally, an introducer can be used to transapically insert the guide wire 104, with attached recapture sleeve 102, through the patient's ventricle and into the aorta 224. A heart valve prosthesis 220 can be similarly introduced to a desired deployment location. Medical imaging can be used to determine whether the heart valve prosthesis 220 is in the proper deployment location, and the heart valve prosthesis 220 can be partially deployed. If the heart valve prosthesis 220 moves distally from the desired deployment location, the recapture sleeve 102 can be used to envelop and collapse the heart valve prosthesis 220, so that it can be repositioned and redeployed or removed from the patient's body.

FIG. 1a demonstrates the need for a recapture sleeve 102. The partially deployed heart valve prosthesis 220 cannot be moved in the proximal direction because of the risk that it will contact the walls of the aortic sinus 226. Neither can enough force be applied to push the heart valve prosthesis 220 in the distal direction back into the capsule 222. However, while maintaining the position of the heart valve prosthesis 220 and the capsule 222, the guide wire 104 can be moved in the proximal direction so that the recapture sleeve 102 moves over the capsule 222 and the heart valve prosthesis 220, forcing the heart valve prosthesis 220 to collapse back down, and possibly into the capsule 222, as both are enveloped by the recapture sleeve 102.

In FIG. 1a, the heart valve prosthesis 220 is partially deployed from the capsule 222 within the aortic sinus 226. As indicated by the arrows, however, the heart valve prosthesis 220 has moved in the distal direction from its intended deployment position. The recapture sleeve 102 is located distally from the heart valve prosthesis 220 and the capsule 222. In this embodiment, the recapture sleeve 102 is radially constrained about the guide wire 104. If the recapture sleeve 102 is needed during the implantation procedure, the opening 110 of the recapture sleeve 102 can be self-expanding, or it can be expanded manually, such as by inflating a balloon inside the recapture sleeve 102.

In FIG. 1b, the recapture sleeve 102 is no longer radially constrained, and a surgeon has moved the guide wire 104 in the proximal direction, as indicated by the arrows. The opening 110 at the proximal end 108 of the recapture sleeve 102 has partially enveloped the capsule 222. Medical imaging can be used to determine the position of the recapture sleeve 102 relative to the capsule 222 and heart valve prosthesis 220. The surgeon can keep the positions of the heart valve prosthesis 220 and the capsule 222 fixed, so as not move them in the proximal direction. By pushing the heart valve prosthesis 220 in the distal direction, the surgeon can provide additional force to collapse the heart valve prosthesis 220 back down, and possibly into the capsule 222, as the recapture sleeve 102 is moved further in the proximal direction.

In FIG. 1c, the surgeon has moved the guide wire 104 further in the proximal direction, thereby moving the recapture sleeve 102 further in the proximal direction as well. The recapture sleeve 102 has enveloped the capsule (not shown) and heart valve prosthesis (not shown), collapsing the heart valve prosthesis. The opening 110 at the proximal end 108 has closed down, either automatically because it is biased in a closed position, or manually, such as by manipulating a drawstring. The recapture sleeve 102, with the capsule 222 and heart valve prosthesis 220 now inside, can be removed from the body by continuing to move the guide wire 104 in the proximal direction. Alternatively, the heart valve prosthesis 220 can be repositioned and then redeployed by moving the guide wire 104, the recapture sleeve 102 and the capsule 222 in the distal direction to uncover the heart valve prosthesis 220.

In certain embodiments, the capsule 222 assists the recapture sleeve 102 in collapsing the heart valve prosthesis 220. In such embodiments, by way of example, the recapture sleeve 102 is pulled in a proximal direction as described above until it envelops the capsule 222 and extends slightly beyond the proximal end of the capsule 222. Then both the recapture sleeve 102 and the capsule 222 can be pulled in the proximal direction to envelop and therefore collapse the heart valve prosthesis 220.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments with modifications as are suited to the particular use contemplated. It is intended that the appended claims be construed to include other alternative embodiments of the invention.

I claim:

1. A heart valve prosthesis recapture device comprising:
   a heart valve prosthesis having a radially compressed configuration and a radially expanded configuration;
   a valve delivery capsule, having a distal end and a proximally facing opening, wherein the valve delivery capsule is configured to maintain the heart valve prosthesis in the radially compressed configuration and wherein distal movement of the valve delivery capsule releases at least a portion of the heart valve prosthesis from therewithin;
   a guide wire disposed through the valve delivery capsule;
   a recapture sleeve including a distal end fixedly attached to the guide wire at a location distal of the valve delivery capsule and a proximal end having an opening along a longitudinal axis of the recapture sleeve,
   wherein with the valve delivery capsule in a position such that the heart valve prosthesis is partially deployed proximal of the valve delivery capsule, the recapture sleeve is configured to be moved proximally from the location distal from the valve delivery capsule over the valve delivery capsule and over the partially deployed heart valve prosthesis to collapse the partially deployed heart valve prosthesis.

2. The recapture device of claim 1, wherein the recapture sleeve comprises a polymeric material or a metal sleeve.

3. The recapture device of claim 1, wherein at least the proximal end of the recapture sleeve is elastic, and wherein an elasticity of the proximal end of the recapture sleeve is greater than an elasticity of the distal end of the recapture sleeve.

4. The recapture device of claim 1, wherein the proximal end of the recapture sleeve is flared radially outward.

5. The recapture device of claim 1, wherein the opening at the proximal end of the recapture sleeve is biased toward a closed configuration.

6. The recapture device of claim 1, wherein the proximal opening further comprises a drawstring element capable of controlling the diameter of the opening.

7. The recapture device of claim 1, wherein an interior surface of the recapture sleeve is lubricated.

8. The recapture device of claim 1, wherein the recapture sleeve comprises:
   a support structure;
   a first covering on the outside of the support structure; and
   a second covering on the inside of the support structure.

9. The recapture device of claim 1, further comprising an attachment element, which interfaces with the distal end of the recapture sleeve and is configured to be fixedly attached to a guide wire.

10. The recapture device of claim 9, wherein the attachment element is a laser cut metal tube configured to be crimped about a guide wire to fix the recapture sleeve to the guide wire.

11. The recapture device of claim 1, wherein the recapture sleeve comprises an expandable tube comprising an expandable fold configured to unfold upon engaging a heart valve prosthesis.

* * * * *